United States Patent [19]

DeLuca et al.

[11] Patent Number: 4,719,205
[45] Date of Patent: Jan. 12, 1988

[54] SIDE-CHAIN UNSATURATED 1-HYDROXYVITAMIN D COMPOUNDS

[75] Inventors: Hector F. DeLuca; Heinrich K. Schnoes; Rafal R. Sicinski; Yoko Tanaka, all of Madison, Wis.

[73] Assignee: Wisconsin Alumini Research Foundation, Madison, Wis.

[21] Appl. No.: 794,325

[22] Filed: Nov. 4, 1985

Related U.S. Application Data

[63] Continuation of Ser. No. 575,116, Jan. 30, 1984, abandoned.

[51] Int. Cl.$^4$ ............................ A61K 31/59; C07J 9/00
[52] U.S. Cl. .................................. 514/167; 260/397.2
[58] Field of Search ...................... 260/397.2; 514/167

[56] References Cited

U.S. PATENT DOCUMENTS

| | | | |
|---|---|---|---|
| 3,907,843 | 9/1975 | DeLuca et al. | 514/167 |
| 4,225,596 | 9/1980 | DeLuca | 514/167 |
| 4,610,978 | 9/1986 | Dikstein et al. | 514/167 |

*Primary Examiner*—Leonard Schenkman
*Assistant Examiner*—Joseph A. Lipovsky
*Attorney, Agent, or Firm*—Howard W. Bremer

[57] ABSTRACT

Novel 1-hydroxylated vitamin D compounds containing a 22, 23-cis double bond in the side chain are provided. The compounds are characterized by an unexpectedly high binding affinity for the protein receptor forecasting their ready applicability as substitutes for vitamin D or various of its metabolites in their various known applications and in the treatment of various metabolic bone diseases.

13 Claims, No Drawings

SIDE-CHAIN UNSATURATED 1-HYDROXYVITAMIN D COMPOUNDS

This invention was made with Government support under NIH Grant No. AM 14881 awarded by the Department of Health and Human Services. The Government has certain rights in this invention.

This application is a continuation of application Ser. No. 575,116, filed Jan. 30, 1984, now abandoned.

TECHNICAL FIELD

The invention relates to biologically-active vitamin D compounds. More specifically, this invention relates to 1-hydroxyvitamin D compounds containing a 22,23-cis-double bond in the side chain.

BACKGROUND

Because of the well-known and clearly established activity of 1α-hydroxyvitamin D compounds in regulating calcium and phosphate homeostasis in the animal or human, there has been interest in the preparation of the natural metabolites and in the discovery of analogs with useful medicinal properties. This has led to the preparation of a variety of compounds (for examples, see DeLuca et al., Topics in Current Chemistry, vol. 83, p. 1 (1979); Ann. Rev. Biochem. 52, 411 (1983); Yakhimovich, Russian Chem. Rev. 49, 371 (1980) some of which, e.g. 1α-hydroxyvitamin $D_3$ (U.S. Pat. No. 3,741,996) or 1α,25-dihydroxyvitamin $D_3$ (U.S. Pat. No. 3,697,559) already find use in medical practice. Interest in such compounds is continuing especially now that it has been recognized that in addition to their classical function as regulators of calcium homeostasis, 1α,25-dihydroxyvitamin $D_3$ and its analog, 1α-hydroxyvitamin $D_3$, also affect cellular differentiation processes and are capable of inhibiting the growth and proliferation of certain malignant cells [Suda et al., U.S. Pat. No. 4,391,802; Suda et al., Proc. Natl. Acad. Sci. USA 80, 201 (1983); Reitsma et al., Nature, Vol. 306, p. 492–494 (1983)]. There is increasing evidence to show, that expression of biological activity by vitamin D metabolites and analogs involves binding to an intracellular receptor protein at some stage of the overall process (see DeLuca et al., supra). High affinity for this receptor protein is thus a prerequisite for high potency, and desirable vitamin D analogs are those which compete effectively with the natural hormone, 1,25-$(OH)_2D_3$, for the receptor binding site.

Known side chain unsaturated vitamin D compounds include the hydroxy derivatives of vitamin $D_2$, namely 25-hydroxyvitamin $D_2$ (U.S. Pat. No. 3,585,221), 1α,25-dihydroxyvitamin $D_2$ (U.S. Pat. No. 3,880,894), 24-hydroxy- and 24,25-dihydroxyvitamin $D_2$ (Jones et al., Arch. Biochem. Biophys. 202, 450 (1980)), 1α-hydroxyvitamin $D_2$ (U.S. Pat. No. 3,907,843) and certain 24-demethylvitamin $D_2$ compounds (U.S. Pat. No. 3,786,062; Bogoslovskii et al., J. Gen. Chem. USSR 48(4), 828 (1978); Chem Abstr. 89, 163848j and 89, 209016s). One example of a compound with a cis-double bond in the side chain is also known (Bogoslovskii et al., supra).

DISCLOSURE OF INVENTION

The novel compounds of the present invention are characterized by the structures A and B shown below:

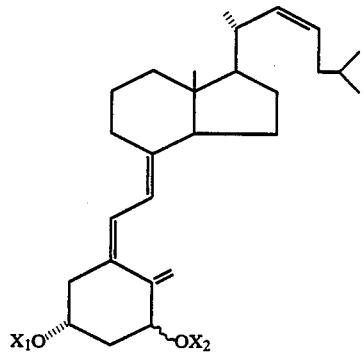

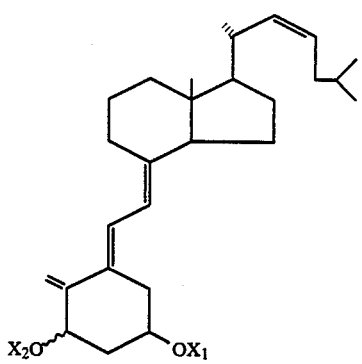

where the hydroxy group (or protected hydroxy group) at carbon 1 may have the α- or β-stereochemical orientation, and where $X_1$ and $X_2$ represent hydrogen or a hydroxy-protecting group, e.g. acyl, alkylsilyl, methoxymethyl or tetrahydropyranyl.

These compounds are thus characterized by a 22,23-cis-double bond (22Z-double bond) in the side chain.

Preferred hydroxy-protecting groups are acyl (alkanoyl) groups of 1 to 6 carbons (e.g. formyl, acetyl, propionyl, butyryl, etc.) or aroyl groups, such as benzoyl, halo- or nitrobenzoyl, or carboxyalkanoyl groups of 2 to 6 carbons, such as oxalyl, malonyl, succinyl, glutanyl or adipyl.

Especially preferred are the compounds of type A above, having a 1α-hydroxy group, because these compounds show unexpectedly high affinity for the receptor protein. These compounds, as 1-hydroxyvitamin D analogs, are related to the known 1-hydroxylated vitamin D compounds, but because of the presence of a 22Z-double bond, were expected to exhibit low, if any, affinity for the receptor since this 22,23-cis-double bond forces the side-chain into a quite different geometry than that assumed by the fully saturated side-chain as it occurs in 1α-hydroxyvitamin $D_3$ or in the natural hormone, 1,25-$(OH)_2D_3$, both compounds of known high affinity for the receptor protein (DeLuca et al., supra). Surprisingly and unexpectedly, it was found, however, that the 1α-hydroxy-22Z-dehydro compounds actually exhibit higher affinity for the receptor than does 1α-hydroxyvitamin $D_3$.

The synthesis of the novel compounds of this invention is summarized by Process Scheme I. In the following description of this process and in the examples, compound designations by numeral (e.g. (1), (2), (3) . . . , etc.) refer to structures so numbered in Process Scheme I, or in the specification.

The starting material for the synthetic process is the diene-protected aldehyde of structure (1) where R is a methoxymethyl group. This starting material is prepared from ergosterol according to the method of Morris et al., (J. Org. Chem. 46, 3422 (1981)). Reaction of compound (1) with a Wittig reagent, having the structure shown below,

in an organic solvent and in the presence of a strong base, provides product (2) featuring the desired 22Z-olefinic side chain.

By removal of the hydroxy-protecting group under acidic conditions, product (2) is converted to compound (3), which is subjected to reduction with a strong hydride reducing agent in an organic solvent to obtain the 5,7-diene sterol, compound (4).

Irradiation of this material, dissolved in an organic solvent, with ultraviolet light converts the 5,7-diene to the corresponding previtamin intermediate, which after isolation and purification is isomerized to the 22Z-dehydro-vitamin $D_3$ analog of structure (5) (R=H) by gentle heating in an organic solvent at a temperature ranging from room temperature to reflux.

The intermediate of structure (5) is a known vitamin D analog, having been prepared previously by Bogoslovskii et al. (J. Gen. Chem. USSR, 48(4), 828 (1978)) by a less convenient procedure.

Intermediate (5) is then converted to the desired final products by 1-hydroxylation using the general method of DeLuca et al. (U.S. Pat. Nos. 4,195,027, 4,260,549). Compound (5) is first tosylated to give the 3β-tosylate of structure (6), which is then solvolyzed in buffered methanol to obtain the novel 3,5-cyclovitamin D intermediate of structure (7) (R=H). This product is then treated with selenium dioxide, and tert.-butylhydroperoxide in an organic solvent, to obtain as the major product the 1α-hydroxycyclovitamin D analog of structure (8), where R is a hydroxy group. It is notable that this allylic hydroxylation at carbon 1 proceeds without complications for a compound like intermediate (7) having the unusual cis-double bond in the side chain with two allylic positions.

The intermediate 1-hydroxycyclovitamin D product is then solvolyzed in glacial acetic acid to obtain in admixture the 5,6-cis and 5,6-trans vitamin D compounds of structures (9) and (10) respectively, having a 3β-acetoxy function. These acetate derivatives (9) and (10) are then separated, and Process Scheme I

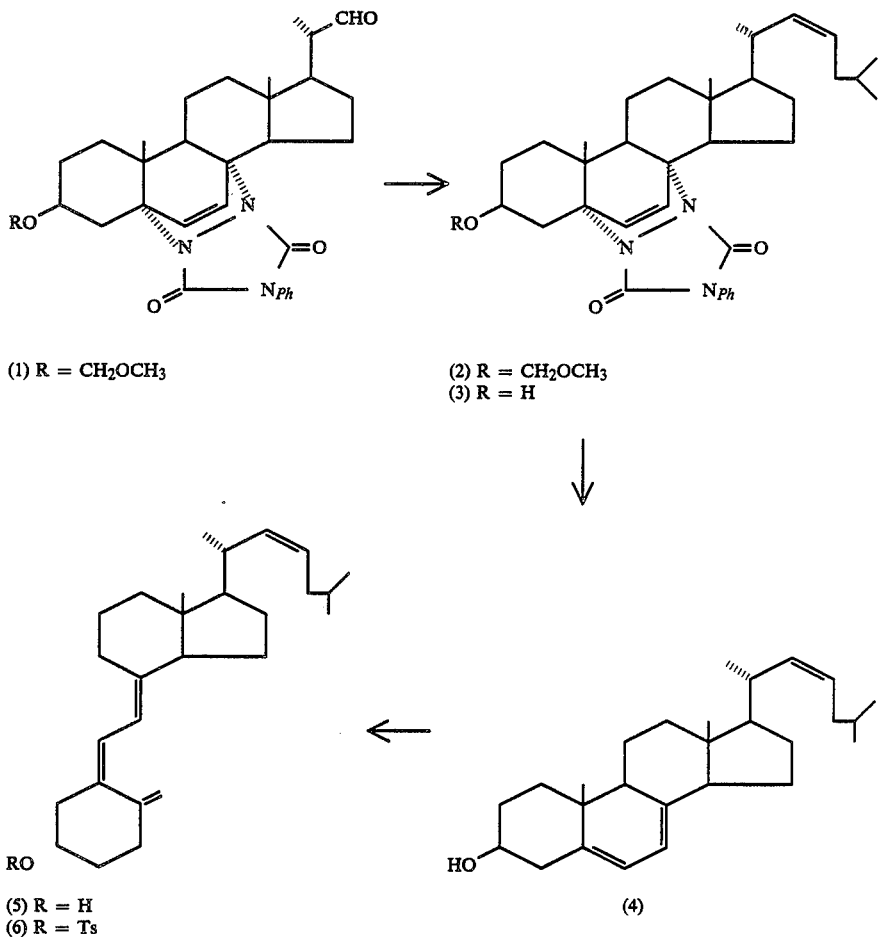

-continued
Process Scheme I

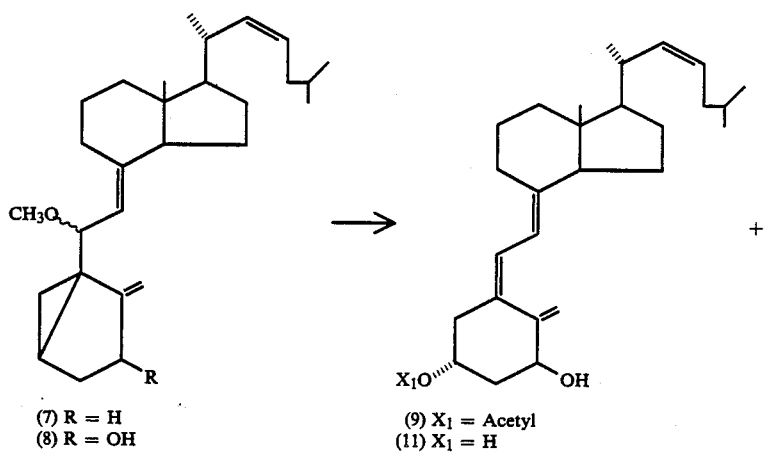

(7) R = H
(8) R = OH (9) $X_1$ = Acetyl
(11) $X_1$ = H

+

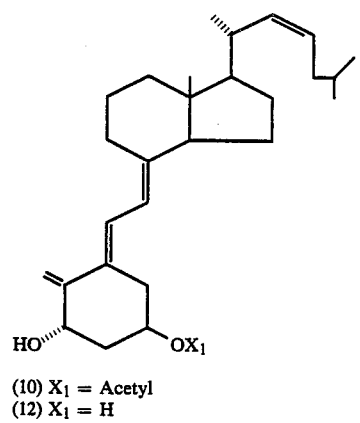

(10) $X_1$ = Acetyl
(12) $X_1$ = H individually hydrolyzed in mild base to produce the desired free diol products, characterized by structures 11 and 12 where $X_1$ represents hydrogen.

It has been found that the 1-hydroxylated cyclovitamin D product described above, of which the 1α-hydroxy-3,5-cyclovitamin D compound of structure (8) is the major component, also contains a small amount of the corresponding 1β-hydroxy-3,5-cyclovitamin D epimer, i.e. the product of structure (13) below. Upon solvolysis in glacial acetic acid, this 1β-hydroxy-epimer gives rise to the corresponding 5,6-cis and 5,6-trans-1β-hydroxy-3β-acetoxy-vitamin D analogs represented by structures (14) and (15), respectively, below, which, if desired, may also be isolated from the solvolysis mixture by chromatography, and then can be separately hydrolyzed in mild base, as described above, to the 1β,3β-diol epimers characterized by structures (16) and (17), respectively.

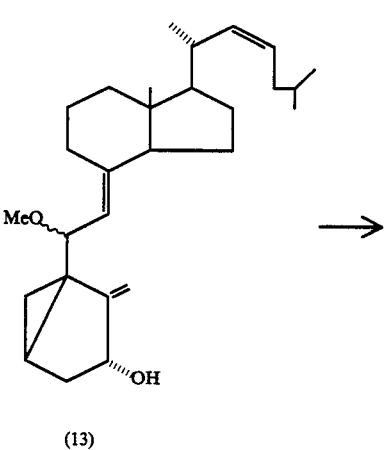

(13)

-continued

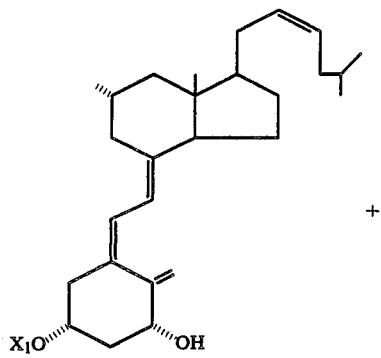

(14) $X_1$ = Ac
(16) $X_1$ = H

+

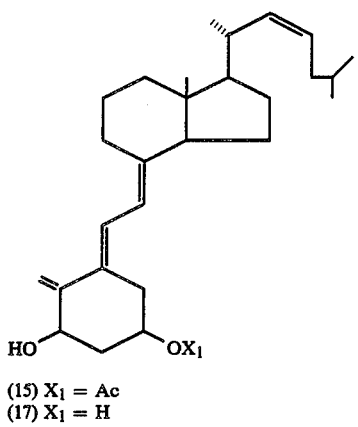

(15) $X_1$ = Ac
(17) $X_1$ = H

In practice, it has been found that the 5,6-trans-1β-hydroxy derivative of structure (15) above, often represents such a minor component of the solvolysis mixture that its direct isolation may be unduly laborious. It is generally more convenient in such cases to prepare 5,6-trans-1β-hydroxy analogs, by the known iodine-catalyzed isomerization process of Verloop et al. (Rec. Trav. Chim. Pays-Bas 78, 1004 (1969)) from the corresponding 5,6-cis compounds. Thus treatment of product (14) with a catalytic amount of iodine in a hydrocarbon or ether solvent gives 5,6-trans product (15), and the analogous isomerization of (16) provides the corresponding trans compound of structure (17).

Acylated derivatives of the products of this invention are readily prepared by conventional methods. Thus, mono-acylates of structures (9), (10) or (14) and (15) result directly from solvolysis; such monoacylates may be further acylated to the corresponding 1,3-diacylates, or desired acylates may be prepared by conventional acylation of the free diols of structures (11), (12) or (16) and (17). It is to be noted also that the 1-hydroxycyclovitamin D intermediates of structure (8) or (13), can be acylated to the corresponding 1-O-acyl derivatives. Subsequent solvolysis of such acyl derivatives in glacial acetic acid, or in an acidic aqueous medium (e.g. according to the method of DeLuca et al., U.S. Pat. No. 4,195,027) yields the 5,6-cis and 5,6-trans 1-hydroxyvitamin D analogs as their 1,3-di-O-acyl or 1-O-acyl derivatives, respectively.

A noteworthy property of the novel compounds of this invention is their high potency as expressed by high binding affinity for the protein receptor. It was assumed that the change in side chain geometry dictated by the presence of a 22,23-cis-double bond (22Z-double bond) would abolish binding affinity, or at least result in a marked decrease in binding affinity, since it is known (e.g. see DeLuca et al., Topics in Curr. Chem., supra) that even subtle changes in stereochemistry (e.g. the change from 24R-hydroxy to 24S-hydroxy) can result in pronounced differences in binding properties, and the compounds were indeed prepared for the purpose of confirming that assumption. Surprisingly, it was found by competitive binding assays (performed according to the protocol of Shepard et al., Biochem. J. 182, 55 (1979)) that the 1α-hydroxy-22Z-dehydro analog of structure (11) exhibits 3-5-fold higher affinity for the receptor protein than does 1α-hydroxyvitamin $D_3$ a known and highly potent vitamin $D_3$ derivative. The other products of this invention exhibit lower but still substantial binding affinity which is in each case higher than that of the corresponding compound featuring a saturated side chain as it occurs in natural metabolites or other known analogs.

Because of this high binding affinity the compounds of this invention can be highly useful substitutes for the known metabolites in the therapy or prophylaxis of calcium disorders such as rickets, hypoparathyroidism, osteodystrophy, osteomalacia or osteoporosis in the human, or related calcium deficiency diseases (e.g. milk fever) in animals. Likewise these compounds may be used for the treatment of certain malignancies, such as human leukemia. Particularly preferred for the above applications is the analog depicted by structure (11) in Process Scheme I, or the corresponding 5,6-trans compound of structure (12) or their acylated derivatives. Suitable mixtures of the above products may also be used in medical or veterinary applications, e.g. the combination of the products represented by structures (11) and (12).

For therapeutic purposes, the compounds may be administered by any conventional route of administration and in any form suitable for the method of administration selected. The compounds may be formulated with any acceptable and innocuous pharmaceutical carrier, in the form of pills, tablets, gelatin capsules, or suppositories, or as solutions, emulsions, dispersions or suspensions in innocuous solvents or oils, and such formulation may contain also other therapeutically active and beneficial ingredients as may be appropriate for the specific applications. For human applications, the compounds are advantageously administered in amounts from about 0.5 to about 10 μg per day, the specific dosage being adjusted in accordance with the specific compound administered, the disease to be treated and the medical history, condition and response of the subject, as is well understood by those skilled in the art.

The present invention is further described in the following detailed description which is intended to be illustrative only and not limiting of the appended claims. In this description the physico-chemical data was obtained using the referenced methods and apparatus. High pressure liquid chromatography (HPLC) was performed on a Waters Associates Model ALC/GPC 204 using a Zorbax-Sil (DuPont) (6.2 mm×25 cm column, flow rate 4 ml/min, 1500 psi). Column chromatography was performed on Silica Gel 60, 70–230 mesh ASTM (Merck). Preparative thin-layer chromatography (TLC) was carried out on Silica 60 PF-254 (20×20 cm plates, 1 mm silica gel). Irradiations were carried out using a Hanovia 608A36 mercury arc lamp fitted with a Vycor filter. All reactions are preferably performed under an inert atmosphere (e.g. argon).

(22Z)-3β-(Methoxymethoxy)-5α,8α-(4-phenyl-1,2-urazolo)cholesta-6,22-dien (2)

Isopentyl phosphonium bromide [(CH$_3$)$_2$CHCH$_2$CH$_2$PPh$_3$Br] (1.67 g, 4.04 mmol) in dry tetrahydrofuran (73 ml) was treated with n-butyllithium (1.7M solution in hexane, 2.42 ml, 4.11 mmol) at 3°–5° C. with stirring. After stirring for 1 h at room temperature, the orange-red solution was cooled to 3° C. and aldehyde (1) (1.84 g, 3.36 mmol) in dry THF (24 ml) was added. The colorless reaction mixture was stirred overnight at room temperature and then poured into water and extracted with benzene. The organic extract was washed with 5% HCl, saturated sodium bicarbonate and water, dried (Na$_2$SO$_4$) and concentrated in a vacuo to an oil, which was purified on a column of silica gel. Elution with benzene-ether (94:6) mixture afforded adduct (2) (1.38 g, 68%) as a foam: NMR δ 0.83 (3H, s, 18-H$_3$), 0.89 and 0.91 (6H, each d, J=6.8 Hz, 26-H$_3$ and 27-H$_3$), 0.97 (3H, d, J=6.8 Hz, 21-H$_3$), 0.98 (3H, s, 19-H$_3$), 3.30 (1H, dd, J$_1$=4.4 Hz, J$_2$=14 Hz, 9-H), 3.38 (3H, s, OCH$_3$), 4.33 (1H, m, 3-H), 4.70 and 4.81 (2H, ABq, J=6.8 Hz, OCH$_2$O), 5.21 (2H, br m, 22-H and 23-H), 6.23 and 6.39 (2H, ABq, J=8.5 Hz, 6-H and 7-H), 7.41 (5H, br m, Ar-H); IR: 1756, 1703, 1601, 1397, 1046 cm$^{-1}$; mass spectrum, m/z 601 (M$^+$, <1%), 426 (4), 364 (61), 349 (16), 253 (18), 251 (18), 119 (PhNCO, 100).

(22Z)-5α,8α-(4-phenyl)-1,2-urazolo)cholesta-6,22-dien-3β-ol (3)

A solution of adduct (2) (601 mg, 1 mmol) and p-toluenesulfonic acid (523 mg, 2.75 mmol) in methanol (20 ml)-THF (12 ml) mixture was stirred for 2 days at room temperature. The reaction mixture was poured into saturated sodium bicarbonate and extracted several times with benzene. Extracts were washed with water, dried (Na$_2$SO$_4$) and evaporated under reduced pressure. Purification of the crude product by column chromatography (benzene ether 70:30 as eluant) gave the hydroxy adduct (3) (550 mg, 99%) as a foam: NMR δ 0.83 (3H, s, 18-H$_3$), 0.89 and 0.91 (6H, each d, J=6.8 Hz, 26-H$_3$ and 27-H$_3$), 0.95 (3H, s, 19-H$_3$), 0.98 (3H, d, J=6.8 Hz, 21-H$_3$), 3.16 (1H, dd, J$_1$=4.4 Hz, J$_2$=14 Hz, 9-H), 4.44 (1H, m, 3-H), 5.22 (2H, br m, 22-H and 23-H), 6.22 and 6.39 (2H, ABq, J=8.5 Hz, 6-H and 7-H), 7.40 (5H, br m, Ar-H); IR: 3447, 1754, 1700, 1600, 1397 cm$^{-1}$; mass spectrum, m/z (557 (M$^+$, <1%), 382 (35), 349 (33), 253 (20), 251 (33), 119 (100), 55 (82).

(22Z)-Cholesta-5,7,22-trien-3β-ol (4)

The adduct (3) (530 mg, 0.95 mmol) was converted to the diene (4) by reduction with lithium aluminum hydride (1 g), in tetrahydrofuran (60 ml) at reflux for 18 h. After conventional work-up, the product was purified by chromatography over silica (benzene-ether 94:6 as eluant) to afford pure diene (4) (290 mg, 76%) after crystallization from ethanol:mp 148°–151° C.; [α]$_D^{24}$=−132° (c=0.9, CHCl$_3$); NMR δ 0.66 (3H, s, 18-H$_3$), 0.90 and 0.91 (6H, each d, J=6.8 Hz, 26-H$_3$ and 27-H$_3$), 0.96 (3H, s, 19-H$_3$), 0.98 (3H, d, J=6.9 Hz, 21-H$_3$), 3.64 (1H, m, 3-H), 5.20 (2H, br m, 22-H and 23-H), 5.39 and 5.57 (2H, ABq, J=6 Hz, 7-H and 6-H); UV λ$_{max}$ 281 nm; IR: 3346, 1463, 1375, 1364, 1067, 1040, 831 cm$^{-1}$; mass spectrum, m/z 382 (M$^+$, 100), 349 (65); 323 (32), 271 (15), 253 (30).

(5Z,7E,22Z)-9,10-Secocholesta-5,7,10(19),22-tetraen-3β-ol (5)

Irradiation of 5,7-diene (4) (150 mg, 0.39 mmol) dissolved in ether (120 ml) and benzene (30 ml) (degassed with argon for 40 min) was performed at 0° C. for 13 min using a UV-lamp and Vycor filter. HPLC (1% of 2-propanol in hexane) of the resulting mixture afforded the previtamin (56.9 mg, 38%) as a colorless oil: NMR δ 0.75 (3H, s, 18-CH$_3$), 0.90 and 0.91 (6H, each d, J=6.7 Hz, 26-H$_3$ and 27-H$_3$), 0.99 (3H, d, J=6.8 Hz, 21-H$_3$), 1.64 (3H, s, 19-H$_3$), 3.90 (1H, m, 3-H), 5.20 (2H, br m, 22-H and 23-H), 5.69 and 5.95 (2H, ABq, J=12 Hz, 7-H and 6-H); UV λ$_{max}$ 261 nm, λ$_{min}$ 234 nm.

Thermal isomerization of this previtamin intermediate (56 mg, 0.15 mmol) in refluxing ethanol (3 h) gave the oily vitamin analog (5) (43 mg, 77%) after separation by HPLC. NMR δ 0.60 (3H, s, 18-H$_3$), 0.89 and 0.90 (6H, each d, J=6.7 Hz, 26-H$_3$ and 27-H$_3$), 0.97 (3H, d, J=6.6 Hz, 21-H$_3$), 3.96 (1H, s, 3-H), 4.82 and 5.05 (2H, each narr. m, 19-H$_2$), 5.20 (2H, br m, 22-H and 23-H), 6.04 and 6.24 (2H, ABq, J=11.4 Hz, 7-H and 6-H); UV λ$_{max}$ 265.5 nm, λ$_{min}$ 228 nm; IR: 3427, 1458, 1379, 1048, 966, 943, 892 cm$^{-1}$; mass spectrum, m/z 382 (M$^+$, 21), 349 (5), 271 (8), 253 (14), 136 (100), 118 (82).

1-Hydroxylation of compound (5)

Freshly recrystallized p-toluenesulfonyl chloride (50 mg, 0.26 mmol) was added to a solution of vitamin (5) (50 mg, 0.13 mmol) in dry pyridine (300 μl). After 30 h at 4° C., the reaction mixture was poured into ice/saturated NaHCO$_3$ with stirring. The mixture was stirred for 15 min and extracted with benzene. The organic extract was washed with saturated NaHCO$_3$, saturated copper sulfate and water, dried (Na$_2$SO$_4$) and concentrated in vacuo to obtain the oily tosylate (6). The crude tosylate (6) was treated with NaHCO$_3$ (150 mg) in anhydrous methanol (10 ml) and the mixture was stirred for 8.5 h at 55° C. After cooling and concentration to ~2 ml the mixture was diluted with benzene (80 ml), washed with water, dried (Na$_2$SO$_4$) and evaporated under reduced pressure. The oily 3,5-cyclovitamin D compound (7) thus obtained was sufficiently pure to be used for the following oxidation step without any purification. To a vigorously stirred suspension of SeO$_2$ (5.1 mg, 0.046 mmol) in dry CH$_2$Cl$_2$ (5 ml), tert-butylhydroperoxide (16.5 μl, 0.118 mmol) was added. After 30 min dry pyridine (50 μl) was added and the mixture was stirred for additional 25 min at room temperature, diluted with CH$_2$Cl$_2$ (3 ml) and cooled to 0° C. The crude 3,5-cyclovitamin product (7) in CH$_2$Cl$_2$ (4.5 ml) was then added. The reaction proceeded at 0° C. for 15 min and then it was allowed to warm slowly (30 min) to room temperature. The mixture was transferred to a separatory funnel and shaken with 30 ml of 10% NaOH. Ether (150 ml) was added and the separate organic phase was washed with 10% NaOH, water and dried over Na$_2$SO$_4$. Concentration to dryness in vacuo gave a yellow oily residue which was purified on silica gel TLC plate developed in 7:3 hexane-ethyl acetate giving 1-hydroxycyclovitamin product (20 mg, 37%): NMR δ 0.59 (3H, s, 18-H$_3$), 0.63 (1H, m, 3-H), 0.89 and 0.90 (6H, each d, J=6.9 Hz, 26-H$_3$ and 27-H$_3$), 0.96 (3H, d, J=6.9 Hz, 21-H$_3$), 3.25 (3H, s, —OCH$_3$), 4.17 (2H, m, 1-H and 6-H), 4.96 (1H, d, J=9.3 Hz, 7-H), 5.1–5.4 (4H, br m, 19-H$_2$, 22-H and 23-H); mass spectrum, m/z 412 (M$^+$, 26), 380 (48), 339 (22), 269 (28), 245 (20), 135 (100). This product is composed chiefly of the 1α-hydroxycyclovitamin D compound of structure (8), as well as small amount of the corresponding 1β-hydroxy-epimer (13). These components may be separated at this stage, if desired, but such separation is not required.

The 1-hydroxycyclovitamin product (18 mg) as obtained above was heated (55° C./15 min) in glacial acetic acid (0.8 ml), the mixture was neutralized (ice/saturated $NaHCO_3$) and extracted with benzene and ether, to yield after HPLC (1.5% of 2-propanol in hexane as eluent) separation pure 3β-acetoxyvitamins (9) (6.60 mg, 34%, eluting at 42 ml), (10) (4.20 mg, 22%, eluting at 50 ml), and (14) (1.44 mg, 7% eluting at 36 ml). Compound (9): NMR δ 0.60 (3H, s, 18-$H_3$), 0.90 and 0.92 (6H, each d, J=7.0 Hz, 26-$H_3$ and 27-$H_3$), 0.97 (3H, d, J=6.8 Hz, 21-$H_3$), 2.04 (3H, s, —$OCOCH_3$), 4.41 (1H, m, 1-H), 5.02 (1H, narrow m, 19-H), 5.1–5.4 (4H, br m, 3-, 19-, 22- and 23-H), 6.03 and 6.35 (2H, ABq, J=11.4 Hz, 7-H and 6-H); UV $\lambda_{max}$ 264.5 nm, $\lambda_{min}$ 227.5 nm; mass spectrum, m/z 440 ($M^+$, 10), 380 (72), 362 (7), 269 (31), 251 (12), 135 (100), 134 (99). Compound (10): NMR δ 0.60 (3H, s, 18-$H_3$), 0.90 and 0.91 (6H, each d, J=7.0 Hz, 26-$H_3$ and 27-$H_3$), 0.97 (3H, d, J=6.9 Hz, 21-$H_3$), 2.05 (3H, s, —$OCOCH_3$), 4.49 (1H, m, 1-H), 5.00 and 5.14 (2H, each narr. m, 19-$H_2$), 5.20 (3H, br m, 3-, 22- and 23-H), 5.82 and 6.59 (2H, ABq, J=12.0 Hz, 7-H and 6-H); UV $\lambda_{max}$ 270 nm; $\lambda_{min}$ 228 nm; mass spectrum, m/z 440 ($M^+$, 4), 380 (30), 269 (10), 135 (100), 134 (52). Compound (14): NMR δ 0.58 (3H, s, 18-$H_3$), 0.89 and 0.90 (6H, each d, J=6.9 Hz, 26-$H_3$ and 27-$H_3$), 0.96 (3H, d, J=6.9 Hz, 21-$H_3$), 2.06 (3H, s, —$OCOCH_3$), 4.16 (1H, m, 1-H), 4.98 (2H, m, 3-H and 19-H), 5.1–5.4 (3H, br m, 19-, 22- and 23-H); UV $\lambda_{max}$ 263 nm, $\lambda_{min}$ 227 nm; mass spectrum, m/z 440 ($M^+$, 32), 380 (78), 362 (21), 269 (28), 251 (19), 135 (100), 134 (82).

Hydrolysis of 3β-acetoxy group in compounds (9), (10) and (14)

Each of the 3β-acetoxy-derivatives (9), (10) and (14) was separately hydrolyzed, using the same procedure. A solution of 3β-acetoxyvitamin (0.7–6 mg) in ethanol (0.1 ml) was treated with 10% KOH in methanol (0.8 ml) and the mixture was heated for 1 h at 50° C. After usual work-up and final HPLC purification (8% of 2-propanol in hexane as eluent) the corresponding 1-hydroxyvitamins were obtained, namely: Compound (11): NMR δ 0.59 (3H, s, 18-$H_3$), 0.89 and 0.90 (6H, each d, J=7.0 Hz, 26-$H_3$ and 27-$H_3$), 0.96 (3H, d, J=6.8 Hz, 21-$H_3$), 4.23 (1H, m, 3-H), 4.43 (1H, m, 1-H), 5.00 (1H, narr. m, 19-H), 5.1–5.4 (3H, br m, 19-, 22-, and 23-H), 6.02 and 6.39 (2H, ABq, J=11.4 Hz, 7-H and 6-H); UV $\lambda_{max}$ 264.5 nm, $\lambda_{min}$ 227.5 nm; mass spectrum, m/z 398 ($M^+$, 21), 380 (8), 287 (6), 269 (7), 251 (5), 152 (36), 134 (100). (Elution volume 39 ml). Compound (12): NMR δ 0.61 (3H, s, 18-$H_3$), 0.89 and 0.91 (6H, each d, J=7.0 Hz, 26-$H_3$ and 27-$H_3$), 0.97 (3H, d, J=6.9 Hz, 21-$H_3$), 4.25 (1H, m, 3-H), 4.51 (1H, m, 1-H), 4.98 and 5.13 (2H, each narr. m, 19-$H_2$), 5.21 (2H, br m, 22-H and 23-H), 5.89 and 6.59 (2H, ABq, J=11.5 Hz, 7-H and 6-H); UV $\lambda_{max}$ 273 nm, $\lambda_{min}$ 229.5 nm; mass spectrum, m/z 398 ($M^+$, 17), 380 (4), 287 (5), 269 (5), 251 (4), 152 (29), 134 (100). (Elution volume 38 ml). Compound (16): NMR δ 0.60 (3H, s, 18-$H_3$), 0.89 and 0.91 (6H, each d, J=7.0 Hz, 26-$H_3$ and 27-$H_3$), 0.97 (3H, d, J=6.9 Hz, 21-$H_3$), 4.10 (1H, m, 3-H), 4.36 (1H, m, 1-H), 5.01 (1H, d, J=2 Hz, 19-H), 5.1–5.4 (3H, br m, 19-, 22- and 23-H), 6.06 and 6.45 (2H, ABq, J=11.3 Hz, 7-H and 6-H); UV $\lambda_{max}$ 262.5 nm, $\lambda_{min}$ 226.5 nm; mass spectrum, m/z 398 ($M^+$, 20), 380 (19), 269 (11), 251 (10), 152 (100) 134 (60). (Elution volume 32 ml).

If desired, the compounds of this invention can be readily obtained by crystallization from suitable solvents such as ethers, hexane, alcohols, and mixtures thereof as will be evident and well known to those skilled in the art.

We claim:
1. Compounds having the formula

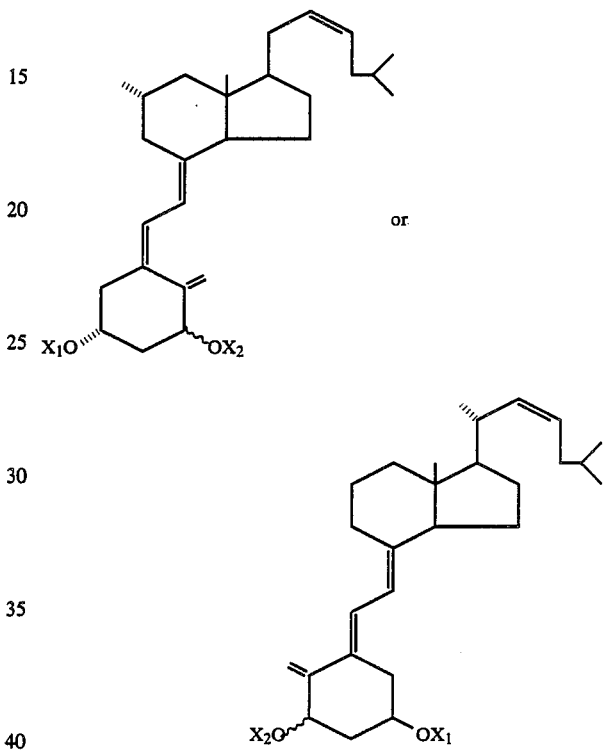

or wherein $X_1$ and $X_2$ is hydrogen or acyl and where the substituent at carbon 1 may have the α or β stereochemical orientation.

2. Compounds according to claim 1 where $X_1$ and $X_2$ are hydrogen.

3. Compounds according to claim 1 wherein at least one of $X_1$ and $X_2$ are acetyl.

4. Compound having the formula

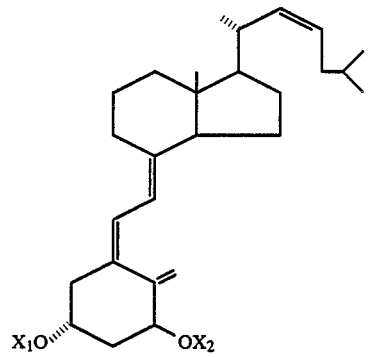

wherein $X_1$ and $X_2$ are hydrogen or acyl.

5. The compound according to claim 4 wherein $X_1$ and $X_2$ are hydrogen.

6. The compound of claim 5 in crystalline form.

7. A pharmaceutical composition comprising the compound of claim 5 together with a pharmaceutically acceptable excipient.

8. A pharmaceutical composition comprising at least one of the compounds of claim 4 together with a pharmaceutically acceptable excipient.

9. Compounds having the formula

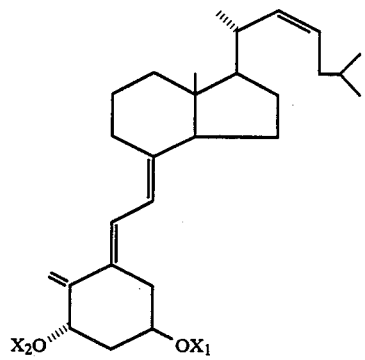

wherein $X_1$ and $X_2$ are hydrogen or acyl.

10. A pharmaceutical composition comprising at least one of the compounds of claim 9, together with a pharmaceutically acceptable excipient.

11. The compound according to claim 9 wherein $X_1$ and $X_2$ are hydrogen.

12. A pharmaceutical composition comprising the compound of claim 11 together with a pharmaceutically acceptable excipient.

13. A pharmaceutical composition comprising in admixture the compounds of claim 5 and claim 11 and a pharmaceutically acceptable excipient.

* * * * *

UNITED STATES PATENT OFFICE
CERTIFICATE OF CORRECTION

Patent No. 4,719,205                    Dated    January 12, 1988

Inventor(s) DeLuca, Schnoes, Sicinski, Tanaka

It is certified that error appears in the above-identified patent and that said Letters Patent are hereby corrected as shown below:

In Process Scheme I, under columns 3 and 4, change from:

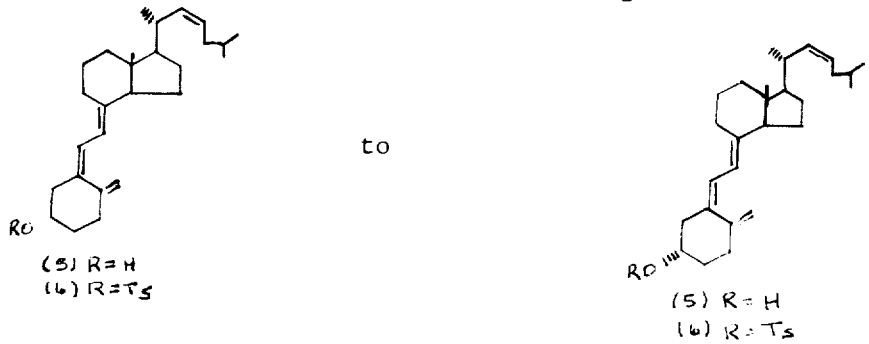

In Process Scheme I, column 7, change from:

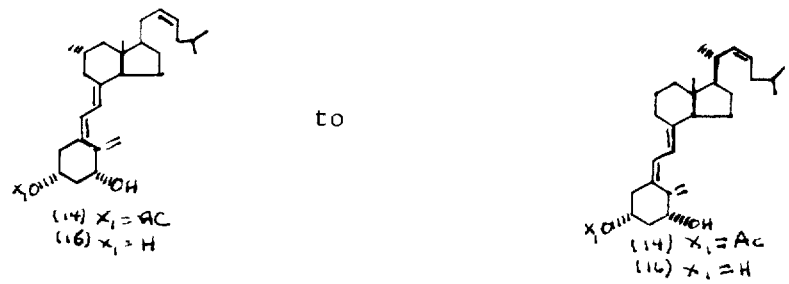

UNITED STATES PATENT AND TRADEMARK OFFICE
CERTIFICATE OF CORRECTION

PATENT NO. : 4,719,205

DATED : January 12, 1988

INVENTOR(S) : DeLuca, Schnoes, Tanaka

It is certified that error appears in the above-identified patent and that said Letters Patent is hereby corrected as shown below:

In Claim 1, first structure, change from:

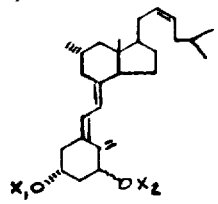    to    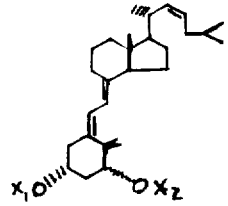

Signed and Sealed this

Eighteenth Day of October, 1988

Attest:

DONALD J. QUIGG

Attesting Officer

Commissioner of Patents and Trademarks